United States Patent [19]

Karger et al.

[11] Patent Number: 4,865,706
[45] Date of Patent: Sep. 12, 1989

[54] HIGH PERFORMANCE MICROCAPILLARY GEL ELECTROPHORESIS

[75] Inventors: Barry L. Karger, Chestnut Hill; Aharon Cohen, Brookline, both of Mass.

[73] Assignee: Northeastern University, Boston, Mass.

[21] Appl. No.: 921,311

[22] Filed: Oct. 21, 1986

[51] Int. Cl.$^4$ ............... G01N 27/28; G01N 27/26
[52] U.S. Cl. ...................... 204/182.8; 204/299 R
[58] Field of Search .................. 204/299 R, 182.8

[56] References Cited

U.S. PATENT DOCUMENTS 4,284,491 8/1981 Vesterberg .............. 204/182.8 X
4,533,307 8/1985 Ansorge .................. 204/180.5 X

FOREIGN PATENT DOCUMENTS 61-11415 5/1986 Japan ....................... 204/299 R

OTHER PUBLICATIONS

Stellam Hjerten "High Performance Electrophoresis: The Electrophoretic Counterpart of High-Performance Liquid Chromatography", J. of Chromatography, 270 (1983) 1-6.

Primary Examiner—John F. Niebling
Assistant Examiner—John S. Starsiak, Jr.
Attorney, Agent, or Firm—Weingarten, Schurgin, Gagnebin & Hayes

[57] ABSTRACT

A microcapillary column for high performance electrophoresis includes a fused silica microcapillary, a gel of crosslinked polyacrylamide polymerized in the tube, and a thin layer of connecting material covalently bonded to the inner surface of the microcapillary wall and to the polymeric gel. The gel-containing microcapillary is prepared by first covalently bonding a suitable bifunctional reagent to the inner surface of the microcapillary wall, and then causing a mixture of monomer, crosslinking agent, and polymerization catalyst to react in the bore of the microcapillary to form a polymeric matrix which is covalently bonded to the microcapillary wall via the bifunctional reagent. In electrophoresis, the gel-containing microcapillary provides peak efficiencies in excess of 100,000 theoretical plates within separation times of less than thirty minutes, and permits trace level determinations of molecular weights.

28 Claims, 7 Drawing Sheets

HIGH PERFORMANCE MICROCAPILLARY GEL ELECTROPHORESIS

FIELD OF THE INVENTION

This invention relates to electrophoresis, and more particularly to gel-containing microcapillary columns for high performance analytical electrophoresis.

BACKGROUND OF THE INVENTION

Electrophoresis is one of the most widely used separation techniques in the biologically-related sciences. Molecular species such as peptides, proteins, and oligonucleotides are separated by causing them to migrate in a buffer solution under the influence of an electric field. This buffer solution normally is used in conjunction with a low to moderate concentration of an appropriate gelling agent such as agarose or polyacrylamide to minimize the occurrence of convective mixing.

Two primary separating mechanisms exist, separations based on differences in the effective charge of the analytes, and separations based on molecular size. The first of these mechanisms is limited to low or moderate molecular weight materials in the case of separations of oligonucleotides because in the high molecular weight range the effective charges of these materials become rather similar, making it difficult or impossible to separate them. In the case of proteins, charge and size can be used independently to achieve separations. Separations based on molecular size are generally referred to as molecular sievinq and are carried out employing as the separating medium gel matrices having controlled pore sizes. In such separating systems, if the effective charges of the analytes are the same, the separation results from differences in the abilities of the different sized molecular species to penetrate through the gel matrix. Smaller molecules move relatively more quickly than larger ones through a gel of a given pore size. Oligonucleotides and medium to high molecular weight polypeptides and proteins are commonly separated by molecular sieving electrophoresis. In the case of proteinaceous materials, however, it is first necessary to modify the materials to be separated so that they all have the same effective charges. This is commonly done by employing an SDS-PAGE derivatization procedure, such as is discussed in "Gel Electrophoresis of Proteins," B. D. Hames and D. Rickwood, Eds., published by IRL Press, Oxford and Washington, D.C., 1981. The contents of this book are hereby incorporated herein by reference.

Most electrophoretic separations are today conducted in slabs or open beds. However, such separations are hard to automate or quantitate. Extremely high resolution separations of materials having different effective charges have been achieved by open tubular free-zone electrophoresis and isotachophoresis in narrow capillary tubes. In addition, bulk flow can be driven by electroosmosis to yield very sharp peaks. Such open tubular electrophoresis is not applicable to the separation of medium to high molecular weight oligonucleotides, however, since these materials have very similar effective charges, as indicated above. In addition, open tubular electrophoresis does not provide size selectivity for proteinaceous materials. The questions thus arise whether electrophoresis on gel-containing microcapillaries can be employed to achieve high resolution separations of oligonucleotides, and whether the conventional procedure of SDS-PAGE can be accomplished on, such microcapillaries. As demonstrated by the present disclosure, the answers to these questions are yes, although given its potential importance as a separating technique in the biological sciences, surprisingly little attention has been paid to microcapillary gel electrophoresis. Hjerten has published an article in the *Journal of Chromatography*. 270, 1–6 (1983), entitled "High Performance Electrophoresis: The Electrophoretic Counterpart of High Performance Liquid Chromatography," in which he employs a polyacrylamide gel in tubes having inside dimensions of 50–300 micrometers, and wall thicknesses of 100–200 micrometers. However, this work suffers from limited efficiency and relatively poor performance due in Part to the use of relatively wide bore capillaries, relatively low applied fields, and high electrical currents. He has also obtained a patent, U.S. Pat. No. 3,728,145, in which he discloses a method for coating the inner wall of a large bore tube with a neutral hydrophilic substance such as methyl cellulose or polyacrylamide to reduce electroendosmosis.

In microcapillary gel electrophoresis, resolution between two compounds is influenced by all the factors which affect band sharpness, including sample size, ionic materials in the samples, and the gel concentration. The latter factor is especially important, since if the gel concentration is too high the analytes are totally excluded from the column, while if it is too low no molecular sieving occurs. No single gel concentration is optimal for the resolution of all mixtures of proteinaceous materials or oligonucleotides. It is necessary to select appropriate gel concentrations for particular samples. Other important variables affecting electrophoresis in microcapillaries are the applied field and the electrical current employed.

The current employed in microcapillary electrophoresis is proportional to the square of the tube radius, and the power dissipated is proportional to the square of the current employed. To keep heating effects low therefore requires low currents, which in turn implies the need to use tubes having as small a radius as reasonably possible.

Regarding the effect of the applied field on the resolution attainable in capillary electrophoresis, Giddings in *Separation Science*, 4, 181–189 (1969) has derived the equation:

$$R_s = \frac{\Delta \mu E \sqrt{t}}{4 \sqrt{2D}}$$

where $R_s$ is the resolution achievable between two components of a mixture, $\Delta \mu$ is the difference in electrophoretic mobility of two consecutive solutes, E is the applied electric field, t is the time for the electrophoretic analysis, and D is the diffusion coefficient of solutes in the medium (generally taken for proteins to be about $10^{-6}$ cm$^2$/sec). As $$t = \frac{L}{E\mu_{ep}}$$

where L is the tubing length and $\mu_{ep}$ is the electrophoretic mobility, substituting in the above equation for t yields $$R_s = \frac{\Delta \mu E^{\frac{1}{2}} \sqrt{L}}{\mu_{ep}^{\frac{1}{2}}(4) \sqrt{2D}}$$

An examination of these equations shows that increasing the applied electric field E should increase the resolution in all circumstances. However, it is elementary that increasing the applied potential also increases the current, which in turn increases the heat which must ultimately be dissipated. Thus in the final analysis, for best resolution one must use the highest applied electric fields consistent with manageable thermal effects. It would therefore be very desirable to have gel-containing microcapillary electrophoresis columns which can tolerate the application of high applied electric fields and which do not suffer too seriously from thermal effects produced by such fields.

SUMMARY OF THE INVENTION

Many of the deficiencies of the prior art are overcome and the above-identified needs are answered by the present invention, which provides a gel-containing microcapillary for high performance electrophoresis. It includes a silica-based microcapillary, a crosslinked polymeric gel in the interior cavity of the microcapillary, and a very thin layer of connecting material between the inner surface of the microcapillary wall and the polymeric gel material, this layer of connecting material being covalently bonded both to the microcapillary wall and to the polymeric gel. A preferred microcapillary construction material is fused silica, and a preferred crosslinked polymeric gel material is a copolymer of acrylamide and N,N'-methylenebisacrylamide. The layer of connecting material between the microcapillary wall and the polymeric gel originates as a bifunctional reagent possessing a first reactive functional group capable of reacting with silanol groups, and a second reactive group which is capable of reacting with vinyl monomers and crosslinking agents which when polymerized constitute the polymeric gel.

The gel-containing microcapillary of the invention is prepared in several stages, as follows: first, a microcapillary is flushed with dry ammonia gas at a predetermined temperature and for a predetermined time, and then this microcapillary is treated with a solution of an appropriate bifunctional reagent. Upon treatment of the activated microcapillary with the solution of this bifunctional reagent, a layer of the bifunctional reagent is covalently attached to the inner surface of the microcapillary wall. Following this operation, unreacted bifunctional reagent is removed and then the coated microcapillary is treated with a solution of at least one monomer, at least one crosslinking agent, and at least one free radical source, and this mixture is allowed to polymerize in the microcapillary tube, ultimately forming a crosslinked polymeric matrix which is covalently bound to the microcapillary wall via tee bifunctional reagent. As a final step, one end of the gel-containing microcapillary is cut off cleanly and squarely.

The gel-containing microcapillaries of the invention are stable and function well under applied electric fields typically of 400 to 500 volts/cm, and with currents typically up to approximately 40 microamperes. Under these conditions, extremely high resolution separations are obtained on very small amounts of material. In addition, the microcapillaries of the invention have been demonstrated to resolve mixtures of analytes as a linear function of the logarithms of their molecular weights. Accordingly, they permit convenient and accurate molecular weight determinations on nanogram or lower amounts of unknown biopolymers.

DESCRIPTION OF THE DRAWING

The invention will be better understood from a consideration of the following detailed description taken in conjunction with the drawing in which.

DETAILED DESCRIPTION OF THE INVENTION

Figure 1:
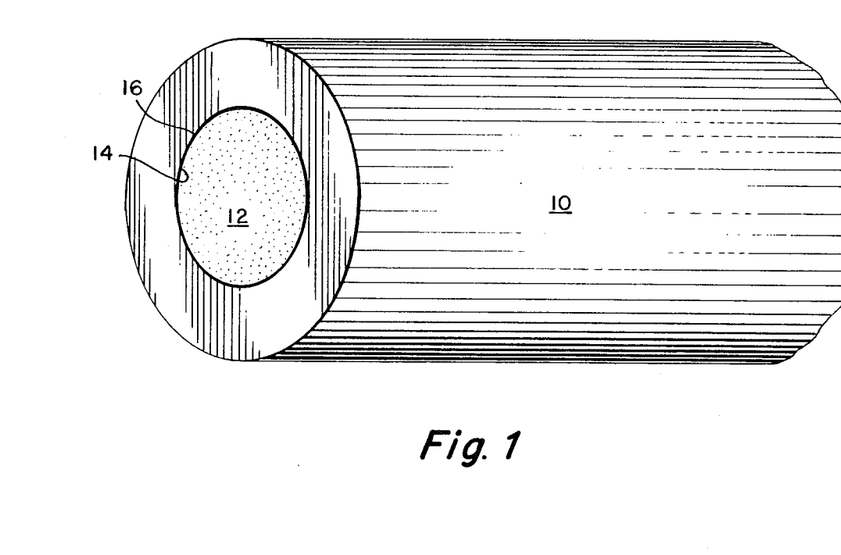
FIG. 1 shows a magnified perspective view of the end of the gel-containing microcapillary of the invention.

As shown in FIG. 1, the gel-containing microcapillary column of the invention includes a silica-based microcapillary 10, a crosslinked polymeric gel material 12 within the bore of this microcapillary, and a connecting layer 14 which is covalently bonded to both the polymeric gel 12 and the inner surface 16 of the microcapillary wall. The silica-based microcapillary may be made of any of a variety of glasses provided that the detection system to be employed in the electrophoresis can function adequately with glass as the microcapillary material. Preferably, the micro- capillary is made of fused silica.

The microcapillary dimensions are quite important, in two respects—first, as the internal diameter of the microcapillary is reduced, the electric current and the resultant heating produced by a particular applied electric field is reduced, and second, the thinner the microcapillary wall can be made, the better heat transfer from the microcapillary is achieved. Thus, it is desirable that the microcapillary have a minimum internal diameter and also a minimal wall thickness. Microcapillaries having an internal diameter range between 10 and 200 micrometers and a wall thickness range less than approximately 40 micrometers work well. A preferred range of internal diameters is 25 to 100 micrometers and a preferred range of wall thickness is 25 to 35 micrometers. Obviously, if the wall thickness is made too small, the microcapillary will be too fragile for practical use.

A polyimide coating on the microcapillary permits easy handling of thin-walled microcapillaries.

The polymeric gel material 12 employed can be any crosslinked polymer which has a pore structure which can be varied by varying the amounts of monomer and crosslinking agent and the reaction conditions. Examples of such polymeric systems are polyacrylamide and mixtures of agarose and polyacrylamide. A preferred polymeric gel material is based on acrylamide and N,N'-methylenebisacrylamide, the N,N'-methylenebisacrylamide serving as a crosslinking agent. Other possible crosslinking agents are N,N'-(1,2-dihydroxyethylene)-bisacrylamide, N,N'-diallyltartardiamide, and N,N'-cystamine-bisacrylamide. Other monomers and other crosslinkers will suggest themselves to those skilled in the art.

The polymerization reaction is preferably initiated with ammonium persulfate and N,N,N',N'-tetramethyleneethylenediamine, though other free radical polymerization initiators may be employed as known by those skilled in the art.

The connecting layer 14 between the polymeric gel and the inner surface of the microcapillary wall is derived from a bifunctional reagent which is capable of chemically bonding both to the microcapillary wall and to the monomeric or crosslinking agents employed in the polymerization reaction which forms the gel material. This bifunctional reagent is generally a molecular chain having appropriate reactive functional groups at its respective ends, though non-chain type molecules having appropriate functionalities will also serve. One end of the bifunctional reagent carries a reactive functional group which can bond chemically to silanol groups on the inner surface of the microcapillary wall. Such reactive functional groups are typically reactive silanes such as trialkoxy silane, trichloro silane, mono, di-, or tri-enolate silanes, and amino silanes, where the silicon atom carries at least one group which may be readily displaced. The opposite end of the bifunctional reagent contains a second reactive functional group capable of forming a covalent bond with the polymeric gel material. Such functional groups include vinyl, substituted vinyl, or any group which upon cleavage yields a free radical, but for practical purposes a vinyl group is preferred because it is then possible to form the polymeric gel in the microcapillary and chemically bond it to the microcapillary wall simultaneously. Representative bifunctional reagents are 3-Methacryloxypropyl-trimethyoxysilane, $CH_2=C(CH_3)-CO_2-(CH_2)_3-Si(OCH_3)_3$ and 3-Methacryloxypropyldimethylethoxysilane, $CH_2=C(CH_3)-CO_2-(CH_2)_3-Si(CH_3)_2OC_2H_5$. Other possible bifunctional reagents are vinyltriacetoxysilane, vinyltri($\beta$-methoxyethoxy)silane, vinyltrichlorosilane, and methylvinyldichlorosilane, this list being intended as illustrative but not exhaustive.

For highest resolution it is necessary that at least the front end of the gel-containing microcapillary be cleanly and squarely cut perpendicular to the axis of the microcapillary. If the surface of the polymeric gel material which is exposed at the end of the microcapillary is uneven, it is impossible to make an injection of a uniform narrow band of sample, with the result that broad peaks are obtained. In practice, the end of the column can be conveniently cut cleanly and squarely perpendicular to the axis of the microcapillary by first forming a tight sheath of TEFLON or other plastic material around the end of the microcapillary and then cutting through this sheath and the microcapillary with a microtome.

The gel-containing microcapillaries of the invention are generally prepared as follows. First, the column is activated by heating it in excess of 100° C. for several hours and then flushing it with dry ammonia gas. In the heating step a temperature of 110° C. to 200° C. may be conveniently employed. The time of such heating can vary from a few hours to overnight or longer. The step of treating with dry ammonia gas is generally conducted for approximately 2 hours at a temperature of approximately 30° C.

The activated microcapillary is then flushed with at least 100 tubing volumes of a solution of the bifunctional reagent to be employed in bonding the column gel to the tubing wall, and then left to react for approximately 2 hours or longer at approximately 30° C. filled with this solution of bifunctional reagent. The solution of bifunctional reagent is prepared in a nonaqueous solvent such as an alcohol, an ether, or a moderately polar halogenated solvent and typically contains between 4 and 50% bifunctional reagent by volume. Representative solvents are methanol, dioxane, and methylene chloride. After the bifunctional reagent has been allowed to react with the inner wall of the microcapillary, excess unreacted bifunctional reagent is removed by rinsing the column with at least 100 tubing volumes of a suitable solvent such as methanol, followed by a further rinsing with at least 100 tubing volumes of water.

Next, separate stock solutions of the monomers, crosslinkers, initiators, and free radical sources for the polymerization reaction are prepared, typically in 7 to 8 molar aqueous urea, though higher and lower concentrations of urea may be used. The concentrations of these reagents are picked such that convenient aliquots of the solutions may be taken and mixed together to form a polymerization mixture having predetermined concentrations of monomer, crosslinker, and polymerization catalysts. Before mixing aliquots of these reagents together, the solutions are separately degassed for at least one hour. This degassing operation may be conducted in any of the several ways known to the art, but basically involves stirring the solutions mechanically or agitating them with ultra sound while simultaneously applying a low vacuum of approximately 20 to 30 millimeters of mercury. The preparation of these solutions is as known to the art, for example, as shown by Hames and Rickwood.

The total concentration of monomer and the concentration of crosslinking agent in these sorts of systems are generally expressed respectively as %T and %C, employing the terminology of Hjerten. For the acrylamide/N,N'-methylenebisacrylamide system preferably employed in this invention, the definitions of %T and %C are given below.

$$\% T = \frac{\text{grams of acrylamide + grams of bisacrylamide}}{100 \text{ milliliters of solvent}}$$

$$\% C = \frac{\text{grams of bisacrylamide} \times 100}{\text{grams of bisacrylamide + grams of acrylamide}}$$

The concentrations of monomer and crosslinking agent are predetermined according to the porosity of the polymeric matrix desired. However, the concentrations of initiator and polymerization catalyst in the reaction mixture must be determined experimentally. This is done by preparing test solutions containing the desired %T and %C, but varying the amount of initiator and polymerization catalyst employed. In the event that SDS-PAGE electrophoresis is contemplated, sodium dodecylsulfate is also included in the reaction mixture in the requisite amount. These test solutions are allowed to polymerize at the temperature at which the electrophoresis is to be performed and the progress of the polymerization reaction is monitored by ultraviolet spectroscopy by observing the decrease in the absorbance of the vinyl double bond. Alternatively, the microcapillary may be observed visually. Levels of initiator and polymerization catalyst are selected which cause the polymerization to be essentially complete in a reasonable time, such as approximately 45 to 60 minutes.

Once the correct reagent concentrations have thus been determined, a fresh mixture of the polymerization reagents is prepared and injected into the microcapillary tube, taking care not to create bubbles. A small ID TEFLON tube is used to connect the microcapillary to the syringe employed to fill the microcapillary. When the microcapillary has been filled with polymerization mixture, the syringe is removed and both ends of the microcapillary are dipped in the "running" buffer, i.e., the buffer to be used for the electrophoresis, and maintained there while the polymerization reaction occurs.

The polymerization reaction is carried out at the temperature which is to be employed for subsequent electrophoresis on the microcapillary column. While the polymerization reaction is occurring, the reaction is monitored separately in an aliquot of the reaction mixture by observing the loss of absorbance due to the vinyl groups by ultraviolet spectroscopy or visually. The polymerization reaction in the column and that in the separate monitor solution are the same. When the test solution indicates the polymerization reaction is essentially over, which should be at a time between 45 and 60 minutes, the reaction is allowed to proceed for approximately another two hours, still maintaining the ends of the microcapillary in "running" buffer and maintaining the temperature as indicated above.

After the polymerization reaction in the microcapillary has gone essentially to completion, the microcapillary ends are removed from the "running" buffer and at least one of them is tightly sheathed with small diameter TEFLON tubing. The TEFLON-sheathed ends of the microcapillary are then cut cleanly and squarely perpendicular to the axis of the microcapillary using a microtome, which cuts through the TEFLON sheathing, the microcapillary material, and the polymeric gel, leaving a very smooth surface of gel material exposed at the end of the microcapillary. The end of the microcapillary which has been thus cut is examined under a microscope to ascertain that the cutting operation in fact produced the requisite flatness of the exposed polymeric gel. If necessary, further cuts can be made until a suitably flat end is produced. Both ends of the microcapillary are generally treated in this fashion, although it is really only necessary to have a square cut end on the front of the microcapillary.

Finally, the column is placed in suitable electrophoresis apparatus and a low electric field of approximately 100 to 150 volts/cm is applied for a period of about one hour. If a very noisy baseline or a zero current condition is obtained, this indicates an improperly prepared column. In this event, a new microcapillary must be prepared.

In employing the gel-containing microcapillary column of the invention in electrophoresis, apparatus and techniques which are generally known to the those skilled in the art of open tube free-zone microcapillary electrophoresis are employed. See, for example, S. Terabi, et al., *Anal. Chem.*, 111-113 (1984); and J. W. Jorgenson and K. D. Lukacs, *Science*, 222, 266-272 (1983). In particular, the sample is injected by the so-called "electrophoretic injection" technique. In this technique, the front end of the electrophoresis microcapillary is dipped into a sample solution containing an electrode of the appropriate polarity and an electric field of approximately 50 to 100 volts/cm is applied for a few seconds to cause electrophoresis of a small amount of the sample solution into the end of the microcapillary. The microcapillary is then transferred back to a solution of "running" buffer, the desired electrophoretic field is applied, and the electrophoresis is carried out in the normal way. To aid in cooling the microcapillary, a cooling jacket is preferably employed around the microcapillary over most of its length, excluding only the front and the rear ends of the microcapillary, which are respectively immersed in buffer solution and connected to the detector of the electrophoretic system. A cooling fluid such as $CCl_4$ is circulated through this jacket and maintained at whatever temperature is desired. Such "active" cooling is more effective in maintaining desired microcapillary temperatures than is air cooling.

A method of performing high resolution molecular sieving electrophoresis for analytical purposes thus includes the steps of electrophoretically injecting an aliquot of a sample containing analytes to be separated into a gel-containing microcapillary column of the invention, applying an electric field of between 400 and 500 volts/cm or higher, allowing a current typically less than about 40 microamperes to pass through the microcapillary, and instrumentally detecting and measuring the separated analytes sequentially as they migrate past the detector.

As discussed below, the gel-containing microcapillaries of the invention have been shown to separate analytes as a function of the logarithms of their molecular weights in a linear fashion. Accordingly, it is possible to determine molecular weights of unknown analytes by comparing their mobilities under standard electrophoretic conditions with a calibration chart plotting the log of the molecular weight of standard materials versus the mobilities of such standard materials.

A method of determining the molecular weight of an analyte therefore is to prepare a gel-containing microcapillary column according to this invention, select standard values of the electrophoretic operating parameters, the applied field being typically between 400 and 500 volts/cm or higher and the current being typically less than about 40 microamperes, electrophoretically injecting onto this microcapillary column an aliquot of a standard solution containing several standard analytes of known molecular weight, applying the selected standard values of the electrophoretic operating parameters to the microcapillary column to separate the standards, measuring mobilities of the known standards under the conditions of the electrophoresis, plotting the log of the molecular weight for each of the standard materials versus its mobility under the standard operating conditions, electrophoretically analyzing an unknown solution on the same column under the same conditions, measuring the mobilities of the analytes contained therein, and finally determining the molecular weights of these analytes from a comparison with the calibration plot.

EXPERIMENTAL SECTION

Acrylamide, N,N'-methylenebisacrylamide, N,N,N',N'-tetramethyleneethylenediamine (TEMED), ammonium persulfate, sodium dodecylsulfate, TRIS buffer, and disodium hydrogen phosphate were all ultrapure or electrophoretic grade materials obtained from Swartz/Mann Biotech of Cleveland, Ohio. Somewhat less pure acrylamide from other sources could be suitably purified by recrystallizing three times and deionizing it by treatment with ion exchange resin. Urea was freshly obtained, and triply recrystallized from water methanol. Proteins and peptides were obtained from the Sigma Chemical Company, St. Louis, Mo., and used as received. Water was triply distilled and deionized. The fused silica microcapillary tubing preferably employed in the invention was obtained from Scientific Glass Engineering Inc. with a range of internal diameters of from 50 to 100 micrometers and a range of wall thicknesses between 25 and 35 micrometers. This company also supplies such tubing in other dimensions. Elemental analyses were performed by Multichem Laboratories Inc. of Lowell, Mass. The narrow bore TEFLON tubing (0.2–0.25 millimeters ID) for filling microcapillary tube was obtained from S. Terabi of Kyoto University, Japan. All solutions were filtered through a nylon 66 or methylcellulose filter membrane having a 0.2 micrometer pore size. Analytical samples were kept frozen at −20° C. prior to use, and aliquots of these samples for experimental work were stored at −4° C. Proteins for SDS-PAGE work were prepared as known to the art.

A Soma S-3207 detector by Instrumentation for Research and Development, Inc., Kingston, Mass., was employed, and was modified for microcapillary work as described in the article by S. Terabi, et al, *Anal. Chem.*, 111–113 (1984). Data were converted to digital form using a Nelson Analytical A/D Interface model 762 SA, and stored using an IBM PC/XT computer. Other equipment known to the art will also serve.

Preparation and Testing of Gel-Containing Microcapillary Having 10% T

Fused silica microcapillary tubing having an ID of 75 micrometers, a wall thickness of 30 micrometers, and a polyimide coating was employed. A 40 to 45 cm length of this tubing was taken for preparation of the gel-containing microcapillary. The polyimide coating was removed from a 1 cm section of one end of the tubing by burning. This end ultimately was ultimately connected to the detector of the electrophoresis apparatus.

The microcapillary tubing was heated overnight at about 120° C. in air, then flushed with dry ammonia gas at about 30° C. for approximately two hours. This and other operations reported herein as being carried out at about 30° C. were conducted at room temperature, which is generally about 30° C. ± about 3° C. Next 100 $\mu$l of a 50% solution of 3-Methacryloxypropyltrimethyoxysilane in methanol were passed through the microcapillary at a temperature of about 30° C., leaving the microcapillary filled with bifunctional reagent solution, the ends of the microcapillary were connected via a short length of TEFLON tubing (also filled with bifunctional reagent solution), and the closed and reagent-filled microcapillary was left overnight at about 30° C. The TEFLON tubing was then removed from one end of the microcapillary, and the microcapillary was flushed successively with 250 $\mu$l each of methanol and water to remove unreacted bifunctional reagent. The coated microcapillary was then installed in the detector of the electrophoresis apparatus, and 15 cm sections of the treated and the untreated microcapillaries were taken for analysis. The treated microcapillary was cut to a length of somewhat greater than 20 cm, and a sheathing of TEFLON was installed on its "front" end.

Buffer solution was prepared by dissolving 1.1 g of TRIS buffer in 100 ml of 7 molar urea solution, adding 0.01 g of EDTA and 0.1 g of sodium dodecyl sulfate, and adjusting the pH to 8.6 by the addition of sodium dihydrogen phosphate.

A solution of acrylamide and N,N'-methylenebisacrylamide was prepared by combining 29 g of acrylamide and 1 g of N,N'-methylenebisacrylamide , in 100 ml of buffer solution, giving a solution having a %T of 30% and a %C of 3.3%.

A solution of ammonium persulfate was prepared by dissolving 0.2 g of ammonium persulfate in 2 ml of the buffer solution.

The solutions of buffer, monomers, and ammonium persulfate were separately filtered through 0.2 micrometer filters and degassed for 2 hours by treating them with ultrasound while applying a vacuum of 20–30 mm of mercury.

Ten ml of the acrylamide-bisacrylamide solution was diluted to 30 ml with buffer solution, giving a final solution having %T=10% and %C=3.3%. One ml aliquots of this solution were experimentally treated with varying amounts of ammonium persulfate solution and TEMED, and polymerization times were monitored to determine the correct amounts of persulfate and TEMED to use. It was ascertained that addition of 2.5 $\mu$l of TEMED and 4 $\mu$l of the persulfate solution gave a polymerization time of about 45 minutes.

A 10 ml aliquot of the acrylamide-bisacrylamide solution was diluted to 30 ml with buffer solution, 2.5 $\mu$l of TEMED and 4 $\mu$l of ammonium persulfate solution were added, and in excess of 50 $\mu$l of this polymerization mixture were forced through the microcapillary until no bubbles were observed exiting the microcapillary. The injection syringe was carefully removed from the TEFLON tubing while continuing the injection, to prevent introduction of bubbles into the microcapillary. Finally, both ends of the microcapillary were immersed in "running" buffer and the polymerization was allowed to proceed at about 30° C. The polymerization of the remainder of the polymerization mixture was externally monitored. After polymerization appeared complete, the system was left for a further two hours to ensure full polymerization, then the microcapillary front end was cut off in a microtome at a microcapillary migration distance (front end to detector) of 20 cm. The final gel-containing microcapillary was evaluated for one hour under an applied field of 100 volts/cm, and found to be satisfactory.

Figure 2:
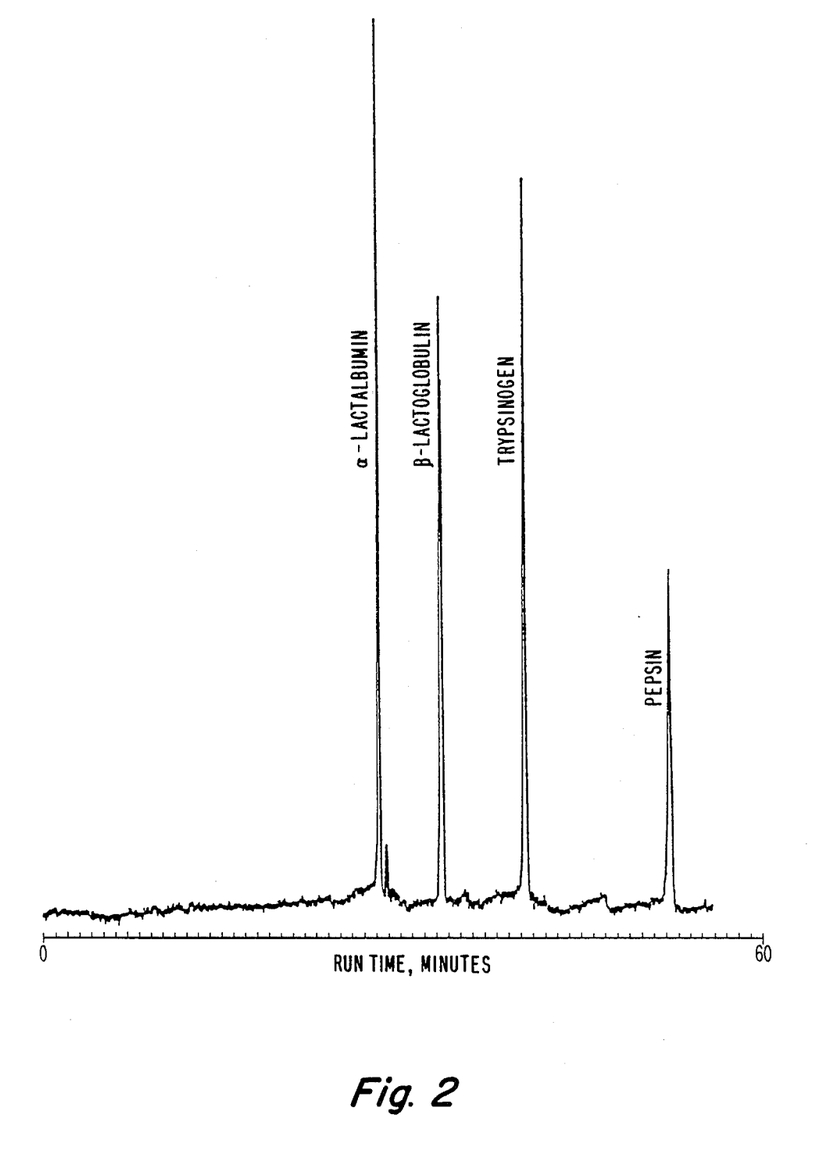
FIG. 2 shows an electropherogram of four standard proteins, α-lactalbumin, β-lactoglobulin, trypsinogen, and pepsin on a gel-containing microcapillary column of the invention containing 10% total monomer, and 3.3% crosslinker. The pH of the buffer was 8.6, and electrophoresis was conducted under an applied field of 400 volts/cm and a current of 24 microamperes, over a 20 centimeter migration distance.

A mixture of four proteins, $\alpha$-lactalbumin, $\beta$-lactoglobulin, trypsinogen, and pepsin, was prepared for SDS-PAGE electrophoresis in the standard manner known to the art, then a sample of this solution was electrophoretically injected onto the microcapillary column by application of an electrical field of 100 volts/cm for 15 seconds. Electrophoresis was conducted at 400 volts/cm and a current of 24 $\mu$A over the 20 cm migration distance. Results are shown in FIG. 2.

Preparation and Testing of Gel-Containing Microcapillaries Having %T=7.5 and 5%

Figure 3:
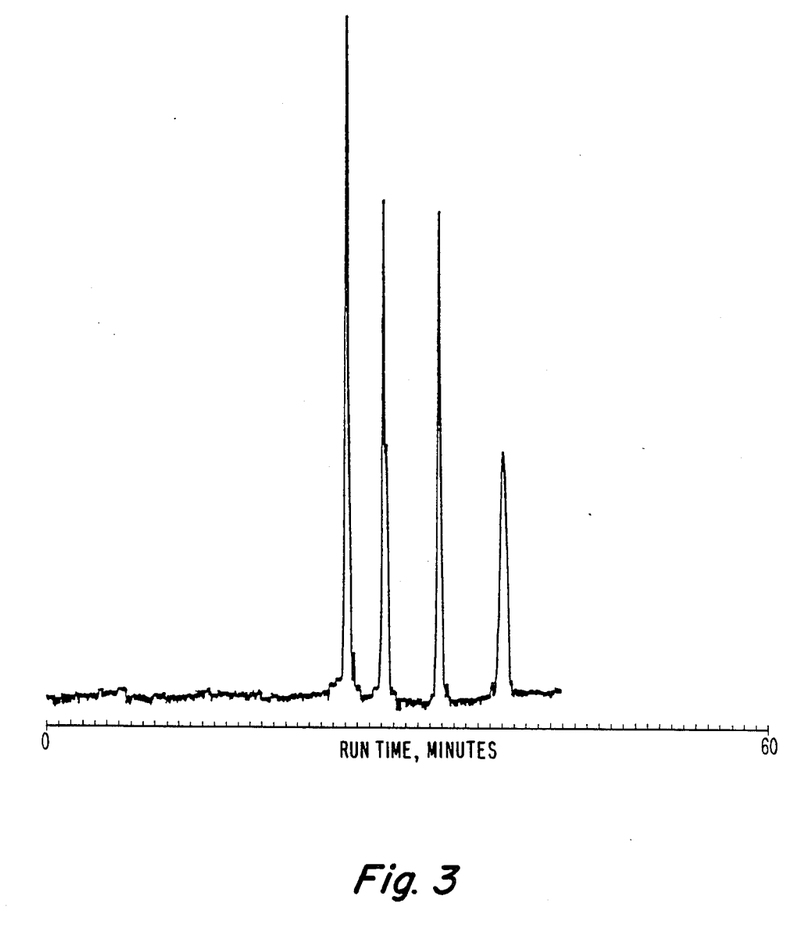
FIG. 3 shows an electrophoretic separation of the same proteins as shown in FIG. 2, under the same electrophoretic conditions except that the column used contained 7.5% total monomers.
Figure 4:
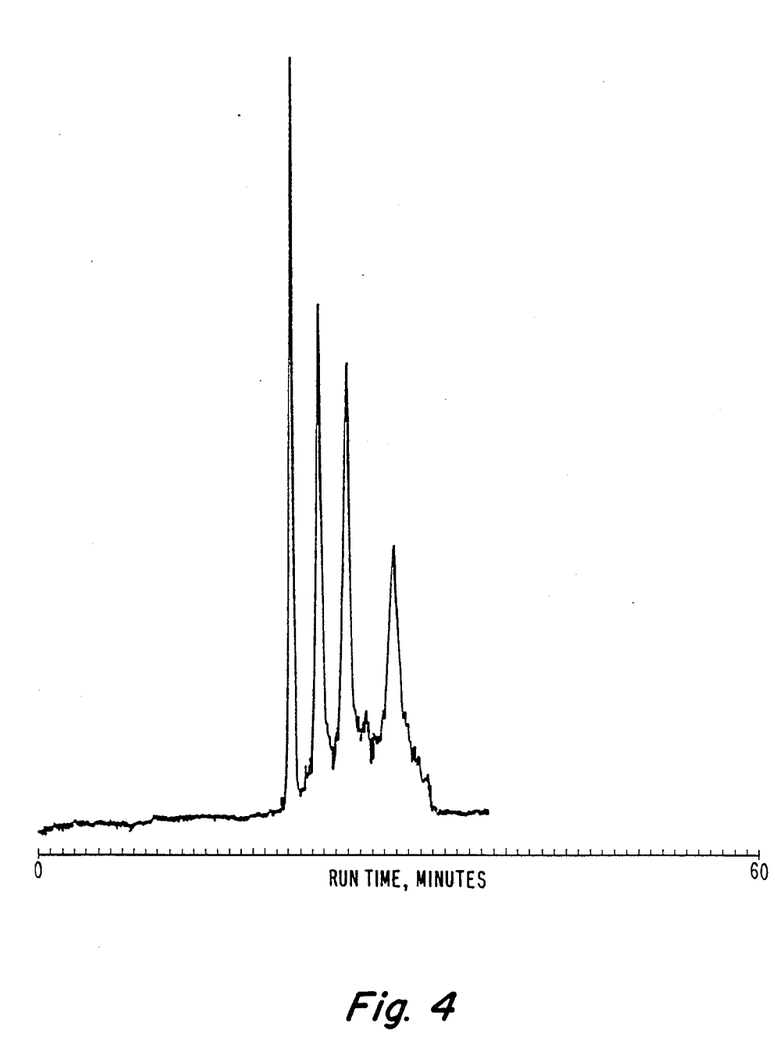
FIG. 4 shows an electrophoretic separation of the same proteins as shown in FIGS. 2 and 3, the electrophoretic conditions again being the same except that in this instance the column contained 5% total monomers.

Other microcapillary columns were prepared exactly as above, except that they possessed gels having %T=7.5% and 5%, respectively, produced by employing appropriately-diluted aliquots of the acrylamide-bisacrylamide stock solution. Mixtures of the same four proteins were separated on these microcapillary columns by electrophoresis under the same conditions as above. Results are shown in FIGS. 3 and 4 respectively.

Figure 5:
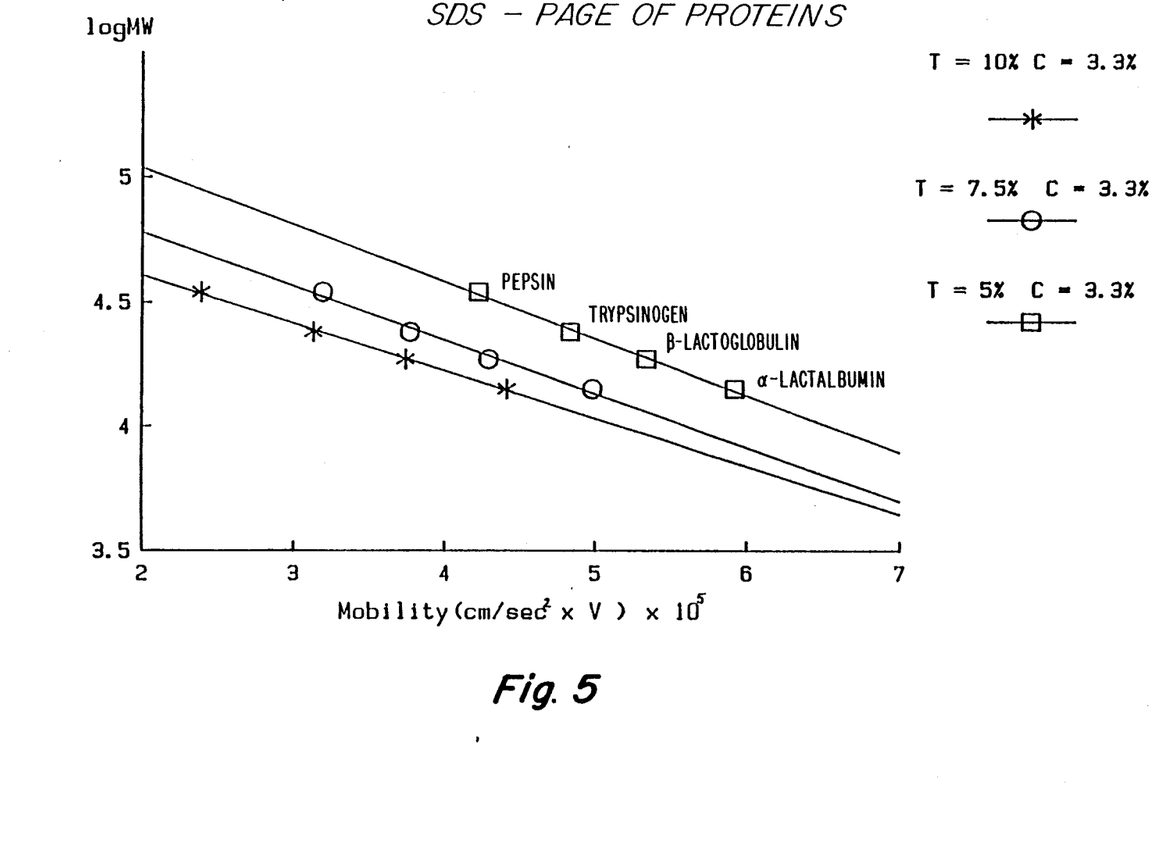
FIG. 5 shows plots of the log of the molecular weight of the tested proteins versus their mobilities on three different microcapillary gel columns of the invention.

Demonstration of Utility of the Gel-Containing Microcapillaries for Molecular Weight Determination In FIG. 5 it is shown that the logarithms of the molecular weights of the tested proteins are a linear function of their mobilities, on each of the gels tested, showing that molecular weight determinations may be performed on the gel-containing microcapillary columns of the invention.

Demonstration of Molecular Sieving

Figure 6:
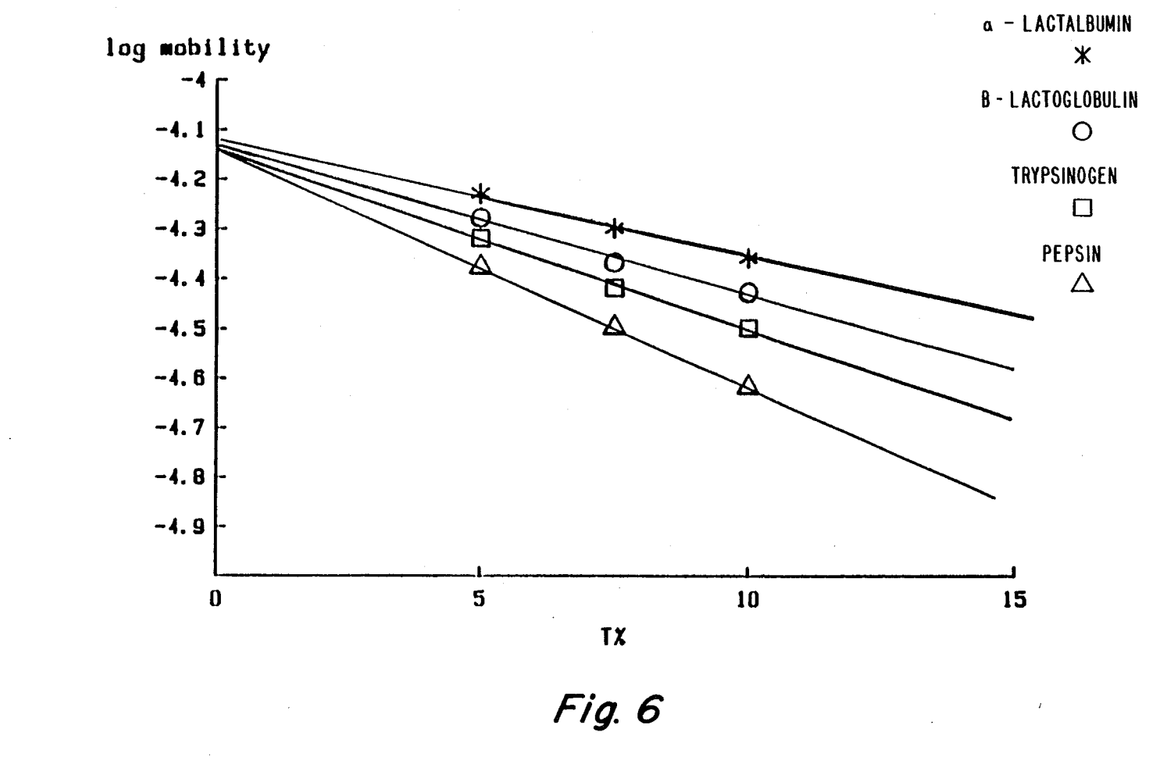
FIG. 6 shows a Ferguson plot of the data from FIGS. 2, 3, and 4.
Figure 7:
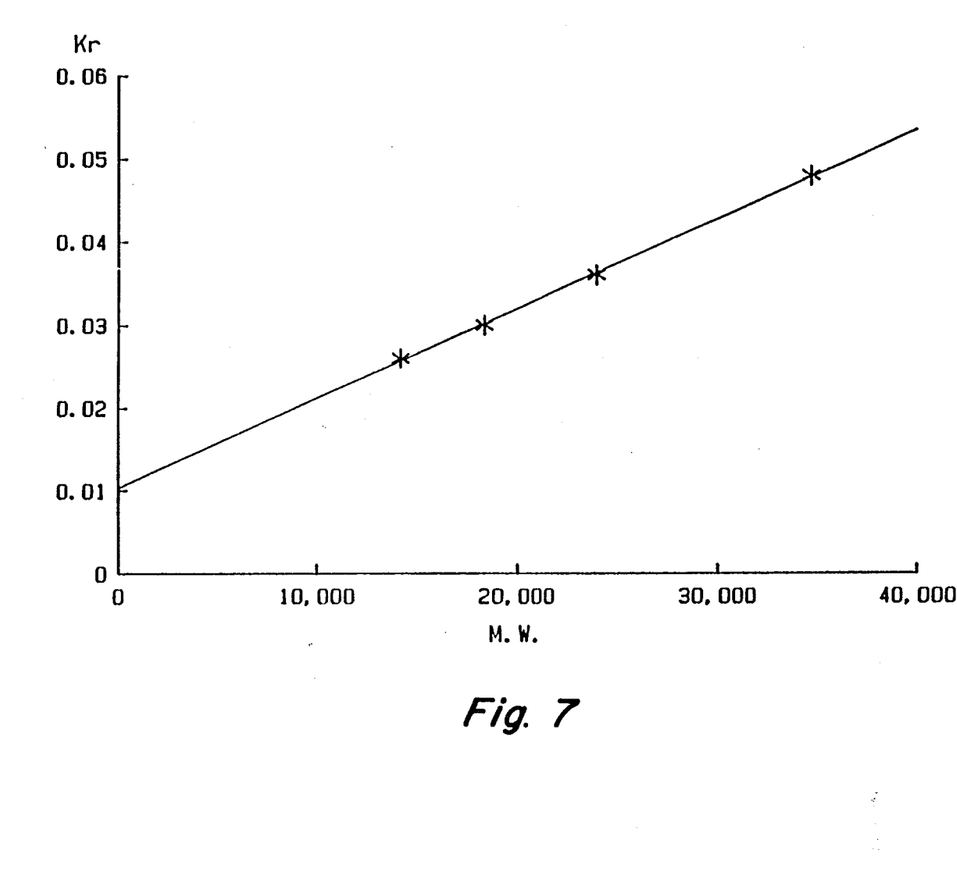
FIG. 7 shows a graph of the Ferguson plot slopes versus molecular weights of standard proteins.

In FIG. 6 the logs of the mobilities of the tested proteins on each of the tested microcapillary columns are plotted versus the %T, in a "Ferguson" plot. In accordance with the behavior expected for molecular sieving separations, the extrapolated mobilities at zero gel concentration of gel are essentially the same. In FIG. 7, the "Ferguson" plot slopes are shown to correlate linearly with the molecular weights of the separated materials, confirming utility of the gel-containing microcapillaries for molecular weight determinations.

What is claimed is:

1. A method for preparing a gel-containing microcapillary column for high performance high precision electrophoresis, comprising:
   flushing a silica-based microcapillary with ammonia gas;
   treating said microcapillary with a solution of bifunctional reagent, said reagent possessing a reactive silane functional group capable of reacting with silanol groups, and a vinyl functionality capable of polymerizing with monomers, to cause covalent bonding of said reagent to the inner surface of the wall of said microcapillary via said reactive silane; and
   treating said microcapillary with a solution containing at least one monomer, at least one crosslinking agent, and at least one free radical source, to cause polymerization, with formation of a crosslinked polymeric gel in the cavity of said microcapillary and covalent binding of said gel to said bifunctional reagent via said vinyl functionality.

2. The method of claim 1 further comprising the step of heating said microcapillary for several hours at a temperature in excess of 100° C. prior to flushing it with ammonia gas.

3. The method of claim 1 wherein said step of flushing with ammonia gas is conducted for at least two hours.

4. The method of claim 1 wherein said step of flushing with ammonia gas is conducted at a temperature of approximately 30° C.

5. The method of claim 1 wherein said step of treating with bifunctional reagent solution is conducted for at least two hours.

6. The method of claim 1 wherein said step of treating with bifunctional reagent solution is conducted at a temperature of approximately 30° C.

7. The method of claim 1 further comprising the step of removing unreacted bifunctional reagent after the step of treating with bifunctional reagent solution.

8. The method of claim 7 wherein said removing step is conducted by flushing successively with methanol and water.

9. The method of claim 1 wherein in said step of treating with a solution of monomer, crosslinking agent, and free radical source, said solution is made up in the buffer to be employed in the electrophoresis, and is degassed.

10. The method of claim 1 further comprising the step of conducting said polymerization of said monomer, crosslinking agent, and free radical source in said microcapillary at the temperature to be employed for electrophoresis on the resulting gel-containing microcapillary.

11. The method of claim 10 wherein in said conducting step both ends of said microcapillary are submerged in said buffer solution during the polymerization reaction.

12. The method of claim 1 wherein in said step of treating with a solution of monomer, crosslinking agent, and free radical source, the concentrations of monomer and crosslinking agent are predetermined and the concentration of free radical source is determined experimentally by varying the concentration of such free radical source in trial solutions and monitoring the polymerization reaction until a concentration of such free radical source is found which causes nearly complete polymerization to occur in approximately 45–60 minutes.

13. The method of claim 1 further comprising the final step of sheathing an end of said microcapillary with TEFLON tubing and cutting it off cleanly and squarely with a microtome.

14. A method for preparing a gel-containing microcapillary column for high performance high precision electrophoresis, comprising:
   heating a silica-based microcapillary for several hours at a temperature in excess of 100° C.;
   flushing said microcapillary with dry ammonia gas;
   treating said microcapillary with a solution of bifunctional reagent, said reagent possessing a reactive silane functional group capable of reacting with silanol groups, and a vinyl group capable of polymerizing with monomers;
   maintaining said solution of bifunctional reagent in said microcapillary for a predetermined time, said treating and maintaining steps causing covalent bonding of said reagent to the inner surface of the wall of said microcapillary via said reactive silane;
   removing unreacted bifunctional reagent;
   filling said microcapillary with a degassed polymerization reagent mixture containing at least one monomer, at least one crosslinking agent, and at least one free radical source at predetermined concentrations, said degassed polymerization reagent mixture being prepared in the buffer to be employed for the electrophoresis;
   allowing said polymerization reagent mixture to polymerize in said microcapillary while controlling the reaction temperature to that temperature which is to be employed for electrophoresis on the resulting gel-containing microcapillary, to cause formation of a crosslinked polymeric gel in the cavity of said microcapillary and covalent bonding of said gel to said bifunctional reagent; and cutting off at least one end of said microcapillary cleanly and squarely.

15. The method of claim 14 wherein said heating step is conducted at a temperature between 110° C. and 200° C.

16. The method of claim 14 wherein said step of flushing with ammonia gas is conducted for at least two hours.

17. The method of claim 14 wherein said step of flushing with ammonia gas is conducted at a temperature of approximately 30° C.

18. The method of claim 14 wherein said bifunctional reagent is selected from the group consisting of 3-Methacryloxypropyltrimethyoxysilane, 3-Methacryloxypropyldimethylethoxysilane, vinyltriacetoxysilane, vinyltri($\beta$-methoxyethoxy)silane, vinyltrichlorosilane, and methylvinyldichlorosilane.

19. The method of claim 18 wherein said bifunctional reagent is 3-Methacryloxypropyltrimethyoxysilane or 3-Methacryloxypropyldimethylethoxysilane.

20. The method of claim 14 wherein said step of treating with a solution of bifunctional reagent is conducted by passing at least 100 microcapillary volumes of said solution through said microcapillary.

21. The method of claim 14 wherein said treating step is conducted at a temperature of approximately 30° C.

22. The method of claim 14 wherein said solution of bifunctional reagent contains between 4% and 50% by volume of said reagent.

23. The method of claim 14 wherein in said maintaining step the predetermined time is at least two hours.

24. The method of claim 14 wherein said removing step is conducted by flushing said microcapillary with a solvent, then with water.

25. The method of claim 24 wherein said solvent is methanol.

26. The method of claim 14 wherein in said polymerization reagent mixture the concentrations of monomer and crosslinking agent are predetermined and the concentration of free radical source is determined experimentally by varying the concentrations of such free radical source in trial solutions and monitoring the polymerization reaction until a concentration of free radical source is found which causes nearly complete polymerization to occur in approximately 45–60 minutes.

27. The method of claim 14 wherein said allowing step both ends of said microcapillary are submerged in the buffer to be employed for the electrphoresis during the polymerization reaction.

28. The method of claim 14 wherein said cutting step is conducted by sheathing and end of said microcapillary with TEFLON tubing, and cutting it off with a microtome.

* * * * *

UNITED STATES PATENT AND TRADEMARK OFFICE
CERTIFICATE OF CORRECTION

PATENT NO. : 4,865,706

DATED : September 12, 1989

INVENTOR(S) : Barry L. Karger, et al.

It is certified that error appears in the above-identified patent and that said Letters Patent is hereby corrected as shown below:

Column 1, line 68, "accomplished on," should read--accomplished on--.

Column 2, line 1, "accomplished on," should read--accomplished on--.

Column 2, line 15, "in Part" should read --in part--.

Column 5, line 20, "employed as known" should read --employed, as known--.

Column 3, line 4, "Anal. Chem., 111-113" should read --Anal. Chem., 56, 111-113--.

Column 9, line 38-39, "Anal. Chem., 111-113" should read --Anal. Chem., 56, 111-113--.

Signed and Sealed this

Second Day of June, 1992

Attest:

DOUGLAS B. COMER

*Attesting Officer*  *Acting Commissioner of Patents and Trademarks*